(12) United States Patent
Schock

(10) Patent No.: US 6,497,678 B2
(45) Date of Patent: Dec. 24, 2002

(54) INTRA-AORTIC BALLOON CATHETER HAVING A VARIABLE DIAMETER INNER TUBE

(75) Inventor: Robert B. Schock, Sparta, NJ (US)

(73) Assignee: Datascope Investment Corp., Montvale, NJ (US)

( * ) Notice: Subject to any disclaimer, the term of this patent is extended or adjusted under 35 U.S.C. 154(b) by 66 days.

(21) Appl. No.: 09/764,831

(22) Filed: Jan. 17, 2001

(65) Prior Publication Data

US 2002/0095115 A1 Jul. 18, 2002

(51) Int. Cl.$^7$ .................. A61M 31/00; A61M 37/00
(52) U.S. Cl. ............. 604/103.06; 604/917; 606/194
(58) Field of Search .................. 604/96.01, 915, 604/914, 917, 921, 264, 523, 524–525, 534, 103, 103.06; 600/16, 18; 606/192, 194, 108

(56) References Cited

U.S. PATENT DOCUMENTS

| 4,362,150 | A |   | 12/1982 | Lombardi, Jr. et al. ..... 128/1 D |
| 5,254,090 | A | * | 10/1993 | Lombardi et al. |
| 5,456,665 | A | * | 10/1995 | Postell |
| 5,759,175 | A | * | 6/1998  | Ariola et al. |
| 6,024,693 | A | * | 2/2000  | Schock et al. |

* cited by examiner

Primary Examiner—Brian L. Casler
Assistant Examiner—LoAn H. Thanh
(74) Attorney, Agent, or Firm—Abraham Ronai

(57) ABSTRACT

An intra-aortic balloon catheter having a variable diameter inner tube.

3 Claims, 2 Drawing Sheets

INTRA-AORTIC BALLOON CATHETER HAVING A VARIABLE DIAMETER INNER TUBE

BACKGROUND OF THE INVENTION

1. Field of the Invention

The invention relates to an improved intra-aortic balloon catheter. More particularly, the invention relates to an intra-aortic balloon catheter having a variable diameter inner tube.

2. Description of the Prior Art

Intra-aortic balloon (IAB) catheters are used in patients with left heart failure to augment the pumping action of the heart. The catheters, approximately 1 meter long, have an inflatable and deflatable balloon at the distal end. The catheter is typically inserted into the femoral artery and moved up the descending thoracic aorta until the distal tip of the balloon is positioned just below or distal to the left subclavian artery. The proximal end of the catheter remains outside of the patient's body. A passageway for inflating and deflating the balloon extends through the catheter and is connected at its proximal end to an external pump. The patient's central aortic pressure is used to time the balloon and the patient's ECG may be used to trigger balloon inflation in synchronous counterpulsation to the patient's heartbeat.

Intra-aortic balloon therapy increases coronary artery perfusion, decreases the workload of the left ventricle, and allows healing of the injured myocardium. Ideally, the balloon should be inflating immediately after the aortic valve closes and deflating just prior to the onset of systole. When properly coordinated, the inflation of the balloon raises the patient's diastolic pressure, increasing the oxygen supply to the myocardium; and balloon deflation just prior to the onset of systole lowers the patient's diastolic pressure, reducing myocardial oxygen demand.

IAB catheters may also have a central passageway or lumen which can be used to measure aortic pressure. Typical dual lumen intra-aortic balloon catheters have an outer, flexible, plastic tube, which serves as the inflating and deflating gas passageway, and a central tube therethrough formed of plastic tubing, stainless steel tubing, or wire coil embedded in plastic tubing. A polyurethane compound is used to form the balloon. In this dual lumen construction, the central lumen may also be used to accommodate a guide wire to facilitate placement of the IAB catheter and to infuse fluids, or to do blood sampling.

Very specialized materials, including NITINOL, a kink-resistant superelastic shape memory metal alloy manufactured and sold by Rayehem Corp, and polyimide, have been used for the inner tube in an effort to reduce its outer diameter. A reduced diameter inner tube allows for a reduced diameter of the folded IAB membrane and thus allows for an easier insertion of the IAB catheter into the patient. The benefits of NITINOL and polyimide include their high kink resistance and flexural stiffness at small wall thicknesses compared to the traditional polyurethane material used for prior art inner tubes.

U.S. Pat. No. 6,024,693, herein incorporated by reference, discloses an intra-aortic balloon catheter having a co-lumen tube in which the inner lumen lies between the inner and outer surfaces of the catheter tube. As disclosed in that application a co-lumen arrangement allows for a reduced size catheter having an increased gas path area.

All IAB catheters have two opposing inner tube design considerations. On the one hand, it is desirable to make the outer diameter of the inner tube as small as possible to ensure the maximum gas passage area for rapid inflation and deflation of the balloon. On the other hand, it is desirable to make the outer diameter of the inner tube as large as possible to: (a) ensure proper stiffness of the catheter for insertion of the catheter into the aorta, (b) maintain the pressure transmitting qualities of the inner tube; and to (c) minimize movement of the catheter during pumping.

U.S. Pat. No. 5,456,665 discloses an IAB having an inner tube made from NITINOL. The use of superelastic shape memory materials is widely known. In general, binary compositions of Nickel (Ni) and Titanium (Ti) yield alloys with shape memory and superelastic properties commonly referred to as Ni—Ti, NITINOL™, and other industry names. Use of NITINOL for the inner tube is desirable because a smaller diameter tube can be used while still maintaining the necessary stiffness. However, NITINOL is very expensive, and therefore, there exists a need for an inexpensive intra-aortic balloon catheter having maximum gas passageway cross section and structural properties adequate to resist excessive movement of the catheter during pumping.

SUMMARY OF THE INVENTION

Accordingly, it is an object of the invention to produce an IAB catheter having an inner tube that is economical to manufacture and that has good kink resistance and flexural stiffness.

It is yet another object of the invention to produce an improved IAB catheter capable of accurate blood pressure measurements.

The invention is an improved intra-aortic balloon catheter with a balloon membrane, a tip, an inner tube, and an outer tube. The portion of the inner tube disposed within the balloon membrane has a larger outer diameter than the portion disposed within the outer surface of the outer tube. The variable diameter inner tube maximizes the cross sectional area of the gas flow passage, i.e. the annular space between the inner tube and the outer tube, while still assuring adequate stiffness of the inner tube to resist excessive movement during pumping.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Figure 1:
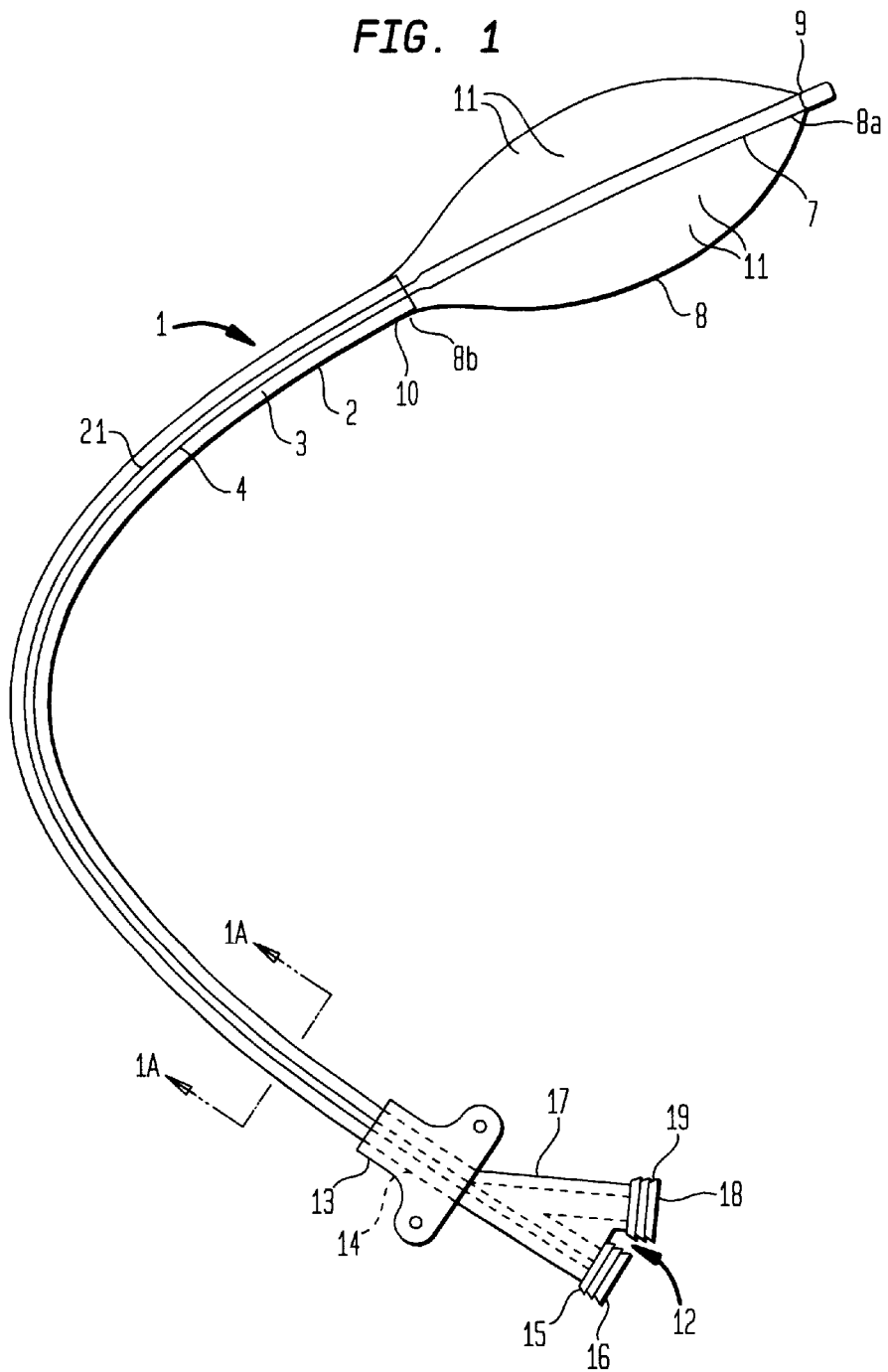
FIG. 1 is a longitudinal cross section of a dual lumen intra-aortic balloon catheter of the present invention.

FIG. 1 illustrates a longitudinal cross section of the catheter of the present invention, generally designated 1.

Figure 1A:
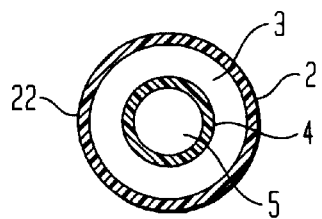
FIG. 1A is a transverse cross section of the catheter of FIG. 1 taken along lines 1A—1A.

Catheter 1 comprises an outer tube 2, forming a gas passageway lumen 3, and a central tube 4 disposed within an outer surface 22 of outer tube 2 and creating a central passageway or lumen 5, as may best be seen in FIG 1A.

Note that the proximal and distal directions are relative to the heart. Therefore, the further distal a portion of a catheter is the closer it is to the heart after insertion of the catheter.

A balloon 8 is disposed at the distal end of catheter 1. A distal portion 7 of central tube 4 extends beyond distal end 10 of outer tube 2. A distal end 8A of the balloon 8 and distal portion 7 of central tube 4 are connected to tip 9. The proximal end 8B of balloon 8 is attached to distal end 10 of outer tube 2. Distal portion 7 of central tube 4 supports the balloon 8. Distal portion 7 must have sufficient strength to prevent inversion of balloon 8 as it inflates and deflates under aortic pressure, but at the same time, be flexible enough to be safely inserted through an introducer sheath, moved through the arterial tree, and maintained in the thoracic aorta.

Balloon 8 is formed of a nonthrombogenic flexible material, such as polyurethane, and may have folds 11 formed as a result of wrapping the balloon 8 about central tube 4 to ease insertion of catheter 1.

Inflation and deflation of the balloon 8 is accomplished through the gas passageway lumen 3. The central passageway or lumen 5 can accommodate a guide wire for placement or repositioning of catheter 1. When the guide wire is not disposed in central lumen 5, central lumen 5 may be used for measuring blood pressure in the descending aorta. This pressure measurement may be used to coordinate the repeated inflation and deflation of balloon 8 with the pumping of the heart, however, use of the patient's ECG is preferred. Additionally, central lumen 5 may be used to infuse liquids into the descending aorta, or to sample blood.

At proximal end 12 of catheter 1 a hub 13 is formed on proximal end 14 of outer tube 2. Central passageway or lumen 5 extends through hub 13 and a connector 16 is provided at proximal end 15 (or exit) of central passageway or lumen 5. Measurement of aortic pressure and blood sampling may be done through proximal end 15 of central passageway 5.

Proximal end 18 of gas passageway lumen 3 exits through a side arm 17 of hub 13 on which is provided a connector 19. Proximal end 18 of central passageway or lumen 5 may be connected to an intra-aortic balloon pump.

Outer tube 1 is preferably made from polyurethane and has a wall thickness of between approximately 0.004 inches (0.10 mm) and 0.012 inches (0.30 mm), and an outer diameter of between approximately 0.079 inches (2 mm) and 0.131 inches (3.3 mm). Alternatively, outer tube 1 may be made from silicone elastomer, EPDM rubber, polyetheramide, or polyvinylchloride.

Central tube 4 is preferably made from polyimide and has a variable outer diameter. Central tube 4 is disposed within an outer surface of outer tube 2. A proximal portion 21 of central tube 4, disposed within outer tube 2, has a wall thickness of between approximately 0.003 inches (0.076 mm) and 0.008 inches (0.20 mm) and an inner diameter of between approximately 0.020 inches (0.51 mm) and 0.035 inches (0.89 mm). Distal portion 7 of central tube 4 disposed within balloon membrane 8 has the same inner diameter measurements as proximal portion 21, however, the wall thickness is between approximately 0.004 inches (0.10 mm) and 0.010 inches (0.25 mm). The outer diameter of the distal portion 7 of central tube 4 should be at least 0.001 inches (0.025 mm) larger than the outer diameter of the proximal portion 21 of central tube 4. The transition in outer diameter between proximal portion 21 and distal portion 7 of central tube 4 is gradual, thus avoiding a stress concentration point. The smaller outer diameter of the proximal portion maximizes the cross sectional area of the gas flow passage, i.e. the annular space between central tube 4 and outer tube 2. The larger outer diameter of distal portion 7 of central tube 4 assures adequate stiffness of central tube 4 to resist excessive movement during pumping. Note that central tube 4 may also be made from nylon, polyurethane, or an appropriate reinforced composite material such as, but not limited to, graphite reinforced polycarbonate.

It may be desirable to attach central tube 4 to an inner surface of the outer tube 2 at one or more points. This improves pushability, stability, pumping speed, and pressure fidelity. Furthermore, as an alternative to, or in addition to varying the diameter of inner tube 123, inner tube 123 may be formed from multiple tubes connected end-to-end having varying material properties, as disclosed in U.S. Pat. No. 6,024,693, assigned to Datascope Investment Corp., herein incorporated by reference.

Figure 2:
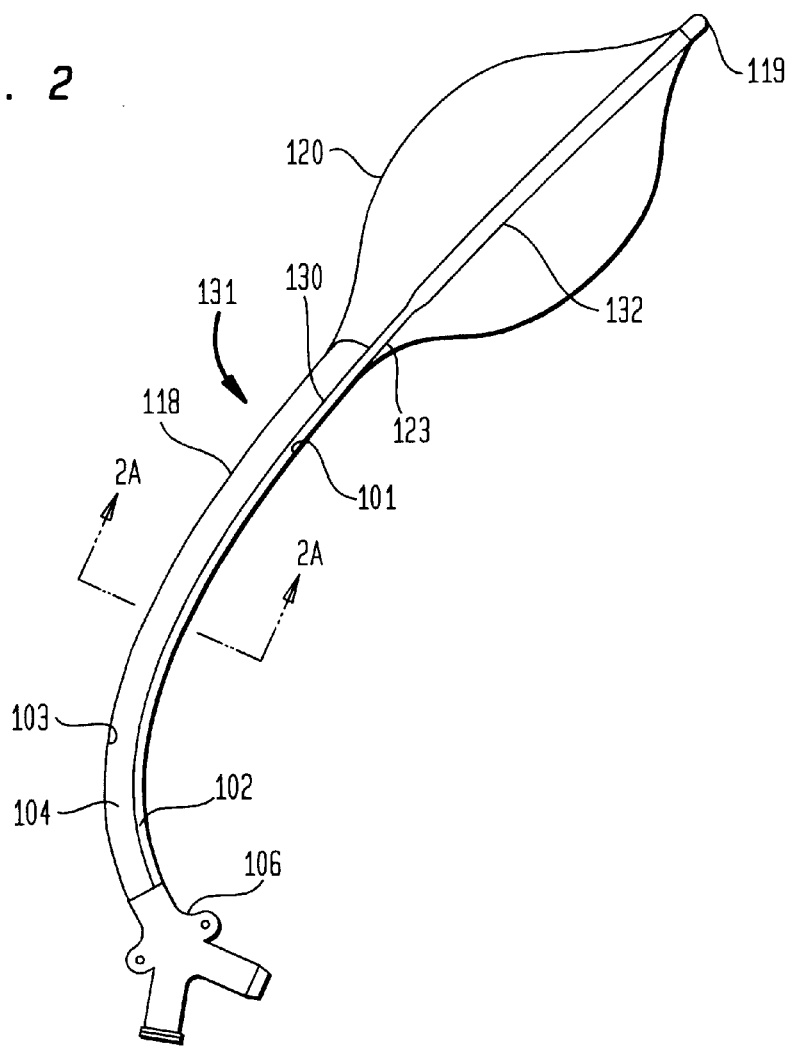
FIG. 2 is a longitudinal cross section of a co-lumen intra-aortic balloon catheter of the present invention.
Figure 2A:
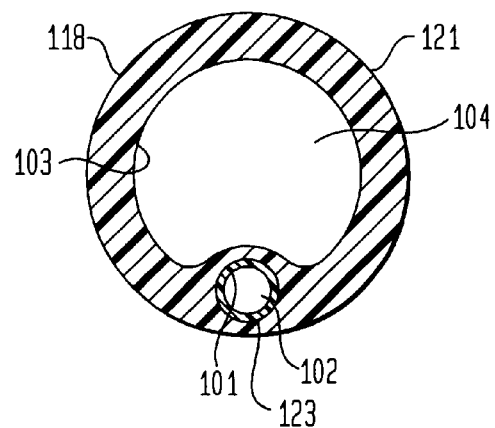
FIG. 2A is a transverse cross section of the co-lumen catheter of FIG. 2 taken along lines 2A—2A.

FIGS. 2 and 2A illustrate a co-lumen intra-aortic balloon catheter, generally designated 131, incorporating a variable diameter inner tube 123. A co-lumen tube 118, having distal and proximal ends, is connected on its distal end to a proximal end of a balloon membrane 120 and on its proximal end to a connector 106. Inner tube 123 extends beyond the distal end of co-lumen tube 118 and is enveloped by balloon membrane 120. A distal end of inner tube 123 is connected to a tip 119 and to a distal end of the balloon membrane 120.

FIG. 2A illustrates a transverse cross section of the co-lumen tube 118, illustrated in FIG. 2 and taken along lines 2A—2A. An outer lumen 104 is defined by a first inner surface 103. An inner lumen 102 is defined by an inner surface 101 of an inner tube 123 extruded together with and embedded in the wall of co-lumen tube 118. Inner tube 123 is disposed within an outer surface 121 of co-lumen tube 118. Inner tube 123 (FIG. 2) extends beyond the distal end of co-lumen tube 118, where it connects to tip 119 and balloon membrane 120 on its distal end, and has a proximal portion 130 and a distal portion 132. The outer diameter of distal portion 132 is larger, or on average larger, than the outer diameter of proximal portion 130. Inner tube 123 may begin to taper up to the diameter of distal portion 132 as soon as it emerges from the distal end of co-lumen tube 118 or it may begin to taper at a more distal point.

Proximal portion 130 of inner tube 123 has a wall thickness of between approximately 0.003 inches (0.076 mm) and 0.008 inches (0.20 mm) and an inner diameter of between approximately 0.020 inches (0.51 mm) and 0.035 inches (0.89 mm). Outer tube section 601 has a wall thickness of between approximately 0.004 inches (0.10 mm) and 0.012 inches (0.30 mm), and an outer diameter of between approximately 0.079 inches (2.0 mm) and 0.131 inches (3.3 mm).

The smaller outer diameter of proximal portion 130 of inner tube 123 maximizes the cross sectional area of outer lumen 104, which serves as the gas flow passage for inflation and deflation of balloon membrane 120. The larger outer diameter of distal portion 132 of inner tube 123 assures adequate stiffness of inner tube 123 to resist excessive movement during pumping.

The co-lumen configuration of co-lumen tube 118 may be formed by either extruding inner tube 123 with a second larger tube (FIGS. 2 and 2A), or alternatively, by adhering inner tube 123 to first inner surface 103 along the length of co-lumen tube 118. Co-lumen tube 118 is preferably made from polyurethane, or alternatively, silicone elastomer, EPDM rubber, or polyetheramide. Inner tube 123 is preferably made from polyimide, or alternatively, nylon, polyurethane, or an appropriate reinforced composite material such as, but not limited to, graphite reinforced polycarbonate. Co-lumen tube 118 and inner tube 123 may be made from the same material, however, it is preferred that co-lumen tube 118 be made from a softer material than inner tube 123.

As an alternative to, or in addition to varying the diameter of inner tube 123, inner tube 123 may be formed from multiple tubes connected end-to-end made from different materials, as disclosed in U.S. Pat. No. 6,024,693, assigned to Datascope Investment Corp., herein incorporated by reference. In one embodiment, disclosed more fully in U.S. Pat. No. 6,024,693, co-lumen tube 118 is extruded having lumens 104 and 102, but without tube 123 (integral formation of both tubes). An inner lumen extension tube is connected to the portion of co-lumen tube 118 defining lumen 102 at its distal end. The inner lumen extension tube, disposed within the balloon membrane, is connected on its opposite end to the balloon catheter tip.

The properly sized inner tube 123 (FIG. 2) or central tube 4 (FIG. 1) has sufficient strength to prevent inversion of the balloon membrane 8 (FIG. 1) or balloon membrane 120 (FIG. 2) as it inflates and deflates under aortic pressure, and at the same time, is flexible enough to be safely inserted through an introducer sheath, moved through the arterial tree, and maintained in the thoracic aorta. Co-lumen tube 118 may be manufactured using an extrusion method, a dip molding process, or any other appropriate method known in the art. Note that an inner surface of inner tube 123 or an inner surface of central tube 4 (FIG. 1) may be lined with a biocompatible polymer, such as TEFLON (TEFLON is a trademark of Dupont Corp.), to reduce friction against the guidewire and improve biocompatibility, or may be lined with a heparin-based coating, such as DURAFLO (DURAFLO is a trademark of Baxter International Corp.), to specifically improve biocompatibility. Furthermore, note that the distal portion of both central tube 7 (FIG. 1) and inner tube 123 (FIG. 2) may taper in diameter down till tip 9 (FIG. 1) or tip 119 (FIG. 2) in order to assure optimal catheter insertability, so long as inner tube 123 is stiff enough to support balloon membrane 120 during pumping.

As many apparently widely different embodiments of the present invention can be made without departing from the spirit and scope thereof, it is to be understood that the invention is not limited to the specific embodiments thereof except as defined in the appended claims. It should be noted that use of the present invention, namely a variable diameter inner tube, although illustrated for use with an intra-aortic balloon catheter, may be used with any type of balloon catheter having similar dual opposing design consideration for the inner tube.

What is claimed is:

1. A balloon catheter comprising an outer tube, a balloon membrane, a tip, and an inner tube disposed within the outer tube and extending beyond a distal end of the outer tube, the tip, a distal end of the inner tube, and a distal end of the balloon membrane are connected, a proximal portion of the inner tube has an inner diameter in the range of 0.020 inches (0.51 mm) to 0.035 inches (0.89 mm) and a wall thickness in the range of 0.003 inches (0.076 mm) to 0.008 inches (0.20 mm) and wherein the distal portion of the inner tube has an inner diameter the same as that of the proximal portion of the inner tube and a wall thickness of at least 0.001 inches greater than that of the proximal portion of the inner tube.

2. A balloon catheter comprising an outer tube, a balloon membrane, a tip, and an inner tube disposed between an outer surface and an inner surface of outer tube and extending beyond a distal end of the outer tube, the tip, a distal end of the inner tube, and a distal end of the balloon membrane are connected, the proximal portion of a inner tube has an inner diameter in the range of 0.020 inches (0.51 mm) to 0.035 inches (0.89 mm) and a wall thickness in the range of 0.003 inches (0.076 mm) to 0.008 inches (0.20 mm) and wherein the distal portion of the inner tube has an inner diameter the same as that of the proximal portion of the inner tube and a wall thickness of at least 0.001 inches greater than that of the proximal portion of the inner tube.

3. The balloon catheter as claimed in claims 1 or 2 wherein the proximal portion of the inner tube has an inner diameter of approximately 0.024 inches (0.61 mm) and a wall thickness of approximately 0.004 inches (0.10 mm) and the distal portion of the inner tube has an inner diameter of approximately 0.024 inches (0.061 mm) and a wall thickness of approximately 0.007 inches (0.18 mm).

* * * * *